United States Patent
Kreiner et al.

(10) Patent No.: US 9,511,159 B2
(45) Date of Patent: Dec. 6, 2016

(54) METHOD AND APPARATUS FOR STERILIZING A SURFACE

(71) Applicant: AT&T Intellectual Property I, L.P., Atlanta, GA (US)

(72) Inventors: Barrett M. Kreiner, Woodstock, GA (US); Jonathan L. Reeves, Roswell, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 108 days.

(21) Appl. No.: 14/322,682

(22) Filed: Jul. 2, 2014

(65) Prior Publication Data

US 2016/0000951 A1    Jan. 7, 2016

(51) Int. Cl.
*A61L 2/00* (2006.01)
*A61L 2/10* (2006.01)
*A61L 2/24* (2006.01)
*H04M 1/17* (2006.01)

(52) U.S. Cl.
CPC ............... *A61L 2/10* (2013.01); *A61L 2/0047* (2013.01); *A61L 2/24* (2013.01); *A61L 2202/14* (2013.01); *A61L 2202/20* (2013.01); *H04M 1/17* (2013.01)

(58) Field of Classification Search
CPC ............ A61L 2/10; A61L 2/24; A61L 2/0047; A61L 2202/14; A61L 2202/20; H04M 1/17
USPC ........................................ 250/455.11, 504 R
See application file for complete search history.

(56) References Cited

U.S. PATENT DOCUMENTS

| 6,278,122 | B1 | 8/2001 | Gagnon |
| 8,125,333 | B2 | 2/2012 | Ressler et al. |
| 8,203,124 | B2 | 6/2012 | Havens et al. |
| 8,226,831 | B2 | 7/2012 | Maiden |

(Continued)

FOREIGN PATENT DOCUMENTS

| CA | 2470170 A1 | 7/2003 |
| WO | WO 2011033263 A1 | 3/2011 |

(Continued)

OTHER PUBLICATIONS

PCT Search Report Application No. PCT/US2015/038831, dated Jan. 15, 2016, pp. 1-13.

(Continued)

*Primary Examiner* — Michael Maskell

(57) ABSTRACT

Various devices for sterilizing a surface are disclosed. For example, a first device includes an ultraviolet light emitting unit, a processor and a computer-readable medium. The computer-readable medium stores instructions which, when executed by the processor, cause the processor to perform operations. The operations include detecting a proximity of a surface to the ultraviolet light emitting unit and activating the ultraviolet light emitting unit to sterilize the surface in response to the detecting. Another device includes an ultraviolet light emitting unit, a processor and a computer-readable medium. The computer-readable medium stores instructions which, when executed by the processor, cause the processor to perform operations. The operations include storing a location parameter, determining whether location information of the device satisfies the location parameter and activating the ultraviolet light emitting unit when it is determined that the location information of the device satisfies the location parameter.

20 Claims, 6 Drawing Sheets

(56) References Cited

U.S. PATENT DOCUMENTS

| | | | |
|---|---|---|---|
| 8,431,910 B1* | 4/2013 | Perry | A61L 2/24 250/455.11 |
| 8,597,569 B2 | 12/2013 | Gruen et al. | |
| 8,662,705 B2 | 3/2014 | Roberts | |
| 8,951,468 B1* | 2/2015 | Perry | A61L 2/10 250/455.11 |
| 2006/0188389 A1 | 8/2006 | Levy | |
| 2006/0261285 A1 | 11/2006 | Broerman | |
| 2007/0102280 A1 | 5/2007 | Hunter et al. | |
| 2011/0158862 A1 | 6/2011 | Kim et al. | |
| 2013/0045132 A1* | 2/2013 | Tumanov | A61L 2/10 422/24 |
| 2013/0323119 A1 | 12/2013 | Alwan | |
| 2013/0323120 A1 | 12/2013 | Ma | |
| 2014/0030144 A1 | 1/2014 | Krosney et al. | |

FOREIGN PATENT DOCUMENTS

| | | |
|---|---|---|
| WO | WO 2012122210 A1 | 9/2012 |
| WO | WO 2013066807 A1 | 5/2013 |
| WO | WO 2013130710 A1 | 9/2013 |
| WO | WO 2014036080 A1 | 3/2014 |

OTHER PUBLICATIONS

"UV-C LEDs", Product Overview, HexaTech, Inc. downloaded Apr. 28, 2014, pp. 1-2; http://www.hexatechinc.com/uv-v-led.html.

"The UVLightBoard Zaps Bacteria From Its Surface as You Type Away", TRENDHUNTER Tech, Apr. 23, 2014, pp. 1-7, http://www.trendhunter.com/trends/uvlightboard.

* cited by examiner

METHOD AND APPARATUS FOR STERILIZING A SURFACE

Embodiments of the present disclosure relate to methods and apparatus for sterilizing a surface. For example, devices and methods of the present disclosure may relate to decontamination and sterilization techniques that provide for the intelligent use of ultraviolet radiation at a frequency that is damaging to pathogens, but safe for humans across a range of devices and other surfaces.

BACKGROUND

Pathogens, comprising bacteria, protozoa and viruses that are infectious agents that cause diseases in humans, are a significant health hazard. The systemic over-use of antibiotics in the treatment of human disease, as well as in our food supply, has created a situation where many previously treatable strains of bacteria are now resistant to nearly all antibiotics. Additionally, there are limited sterilization treatments for viruses and environmental protozoa that do not themselves have significantly negative health impact on people. Various commonly handled objects provide vectors, routes for a pathogen to move from one person to another, for the growth and transmission of these pathogens. This happens as one person who is harboring or shedding a pathogen touches an object, and then another person later touches it, or when the same person touches it at a later time and the pathogen has increased on the object in the intervening time. Seemingly personal items such as credit cards, computer keyboards, computer mice, remote controls, stationary and mobile phones, vehicular steering wheels are actually handled by other individuals, only infrequently. Obviously shared items such as point-of-sale registers, kiosks, intelligent advertisement or other multi-user high touch systems, physical money, door handles and knobs, shopping cart surfaces, are by their function touched by many people frequently. These objects all have the potential to harbor and support the growth of pathogens for a period of time once exposed to the environment and/or touched by humans. It has been well recognized that the broad spectrum ultraviolet (UV) light, commonly found in sunlight, is effective in sterilization, preventing a pathogen from infecting a host, because UV light penetrates the pathogens' smaller cells, or virus virions, and damages the DNA of the pathogen, effectively killing it directly or preventing it from reproducing.

SUMMARY

The present disclosure describes devices and methods for sterilizing a surface. For example, in one embodiment, a device includes an ultraviolet light emitting unit, a processor and a computer-readable medium. The computer-readable medium stores instructions which, when executed by the processor, cause the processor to perform operations. The operations include detecting a proximity of a surface to the ultraviolet light emitting unit and activating the ultraviolet light emitting unit to sterilize the surface in response to the detecting.

In another embodiment, the present disclosure describes a device that includes an ultraviolet light emitting unit, a processor and a computer-readable medium. The computer-readable medium stores instructions which, when executed by the processor, cause the processor to perform operations. The operations include storing a location parameter, determining whether the device satisfies the location parameter and activating the ultraviolet light emitting unit when it is determined that the device satisfies the location parameter.

In another embodiment, the present disclosure describes a method for sterilizing a surface. For example, the method may include receiving, by a processor of a device, a location parameter, determining, by the processor, whether location information of the device satisfies the location parameter and activating, by the processor, an ultraviolet light emitting unit to sterilize the surface when it is determined that the location information of the device satisfies the location parameter.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

Figure 1:
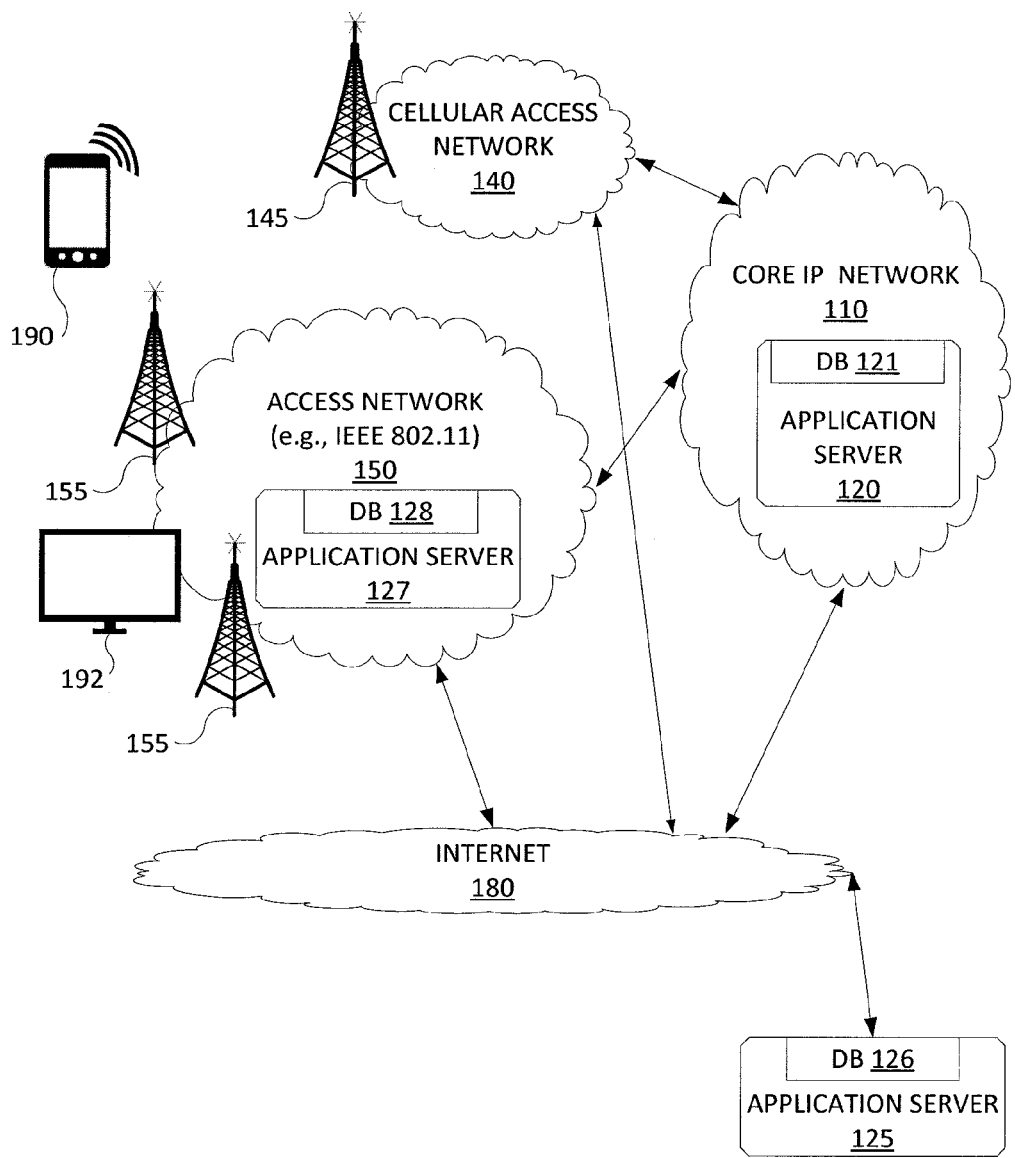
FIG. 1 illustrates an exemplary network related to the present disclosure.

Embodiments of the present disclosure describe devices for sterilizing surfaces using ultraviolet (UV) light, where such devices intelligently determine when to emit the UV light based upon a detection of a presence of a surface, e.g., a portion of a human body, either touching or near to the device, a determination that the device is present at a particular location, e.g., one that is known to be a point of disease transfer, and so forth. In this disclosure, intelligence is identified as a set of inputs, processed by rules, which are used to control what, when, where and how an object is sterilized. Exemplary devices may employ at least one light-emitting diode (LED) or other UV light source emitting a specific frequency in the UV-C range that disrupts reproduction of smaller pathogens, e.g., viruses, bacteria and protozoa, but is non-damaging to larger human cells. In one example, an exemplary device comprises any device having a LED backlit screen, such as a touch-screen or tablet computer, a smart phone, an LED television and so forth. These and other features of the present disclosure are described in greater detail below and in connection with FIGS. 1-7.

Various common items in daily use provide vectors for the growth and transmission of pathogens. For example, point-of-sale registers, credit cards, physical money, door handles and door knobs, computer keyboards, computer mice, remote controls, stationary and mobile phones, shopping cart surfaces, car steering wheels and so forth may all harbor and support the growth of pathogens. The ultraviolet (UV) light in sunlight is an excellent sterilizer, because it penetrates single-cell bacteria and protozoa, and disrupts the DNA, effectively killing or preventing the bacteria from reproducing. UV light is also effective in disrupting the replication of viruses. On the other hand, other cells, including human epidermis cells, are also susceptible to damage from the UV light. UV light is divided into multiple bands. The UV-C band has shorter wavelengths, which is more damaging to pathogens, but does not penetrate larger cells like the longer length UV-A and UV-B bands, including human epidermis cells, which can lead to cancer. For example, light in a certain portion of the UV-C range (e.g., at or around 207 nanometers), is able to penetrate the smaller bacteria and protozoa cells, as well as virions (virus particles) but does not penetrate larger human cells. Accordingly, embodiments of the present disclosure utilize one or more UV light sources capable of emitting light in this particular range.

Many display screens and touch-screen technologies are backlit with light-emitting diodes (LEDs). LEDs have a unique feature that LEDs generate a specific frequency of light. "White" LEDs actually comprise several emitters combined to approximate white light from distinct single frequency lights. Accordingly, in one embodiment, a UV LED emitting UV light, e.g., at or around 207 nm, is included in a display/touch screen, either as part of a "white" LED combination, or as a separate element. Accordingly, when the UV LED is activated, the backlit surface can be sterilized, or the pathogen load on the surface can be reduced. In addition, since touch-screens are by definition touched, the fingers touching the surface will also have a reduced transmittable pathogen load when the UV LED is activated when the fingers are touching the touch-screens as the direct contact with the lit surface will convey more light than through an air gap. Since fingers/hands are the way most humans interact with their environment, they are also the most common way to spread pathogenic illness. Thus using a touch device enabled with UV LED will actually clean the fingers that traditionally were the vectors for pathogen transmissions.

It should be noted that although various examples are described herein in connection with touch-screen devices, embodiments of the present disclosure broadly include many different types of devices and surfaces. For instance, various devices in everyday use include LED backlight displays, such as mobile phones, smart phones, personal digital assistants (PDAs), tablet computers, laptop computers, desktop computers, LED televisions, and so forth. Such devices may also include an LED-based external light, e.g., for use as a flashlight function or in connection with a digital camera. Various other devices may customarily include LED lights, whether in a backlighting arrangement or in another configuration, such as a computer keyboard, a computer mouse, a computer monitor, an overhead light or other component of a motor vehicle, an airplane and the like, a cash register, a point-of-sale device (e.g., for swiping a credit card), and so forth. In addition, in accordance with the present disclosure, various other non-computing devices and surfaces may be equipped with at least one UV LED, e.g., emitting at 207 nm for sterilization purposes. For example, a door handle, a door knob, a surface of a counter or a desk, a steering wheel, and so forth may all be outfitted with at least one UV LED in one embodiment.

In one embodiment, exemplary devices of the present disclosure do not emit UV light at all times, both for safety and power consumption reasons. For example, a surface may need only occasional activation of the UV light to keep the surface decontaminated while not being actively used. In one embodiment a UV LED is capable of varying the light intensity from very intense to completely off. In addition, the UV-C range, and light at the wavelength of 207 nm in particular, is well above what humans can see. Thus, in one example the intensity of the light may be specifically increased when a device or surface is being touched to maximize the decontamination of the skin, e.g., the skin of a human hand touching the surface. Furthermore, some touch devices are held up to areas of the body continuously, like the face, so a short activation followed by a turn-off of the UV LED would be appropriate in this case, or in similar circumstances.

As mentioned above, this novel approach can be further extended beyond touch-screen devices to surfaces that are backlit but not touched, such as LED televisions (TVs), laptop/portable computers and lighting. An LED light may comprise a UV LED source and/or have a UV LED embedded therein. As such, in one embodiment the LED light can emit UV light when appropriate, such as at night or in the dark where it would be more effective. Similarly, an LED TV can send out UV light intermittently while on or off. In one example, a smart LED TV can detect when someone is present or not (broadly when people are proximate to the television unit), and can emit long interval, low intensity light when people are around, and high intensity short interval light when people are not proximate to the television unit. Since TVs are generally deployed in areas where humans congregate, this increases the efficacy of the disinfection. For instance, in many hospital rooms and waiting areas, there is at least one TV available which can be used to provide disinfection not only of surfaces of the TV itself, but of any surfaces which are exposed to the UV light emitted by the TV.

In one embodiment, one or more of the above described features may comprise default settings which may be overridden depending upon the circumstances. For example, in the summer, when pathogen load is naturally lower, less intense/less frequent treatments may be more desirable (e.g., to achieve adequate disinfection performance while minimizing energy usage). Conversely in the winter, when people are inside more often and there is less natural disinfection, increasing the intensity/duration of UV light may be more appropriate to provide adequate disinfection.

Certain locations such as hospitals, gyms, schools, and prisons, are naturally high in pathogen loads due to high concentration of individuals congregating in small areas for an extended period of time. Touch devices are increasingly being mandated for hospital settings, and are continuously touched by hospital staff and patients. In addition, hospital staff and patients may also bring their personal devices into this setting, thereby increasing the risk of contracting and harboring pathogens on the surfaces of such devices. Accordingly, in one example a geographic feature, e.g., geofencing, may be deployed to determine whether and how often to activate the UV disinfection feature of a device. For example, a device aware that it is entering into a location or that it is present at a location could activate a UV LED more frequently and/or use greater intensity light when at or near the location to protect the user and the community. In one example, a device may determine its location based upon a connectivity to and/or a detection of a wireless signal from a particular wireless beacon (e.g., a WLAN access point, a RFID tag, a Bluetooth and/or Bluetooth Low Energy (BLE) beacon, a ZigBee access point, a cellular base station, and the like), based upon global positioning system (GPS) information, and so forth.

Additionally, exemplary devices of the present disclosure may alter a UV light activation/disinfection schedule based on other external factors, such as an alert from a local health authority. For example, a device may be capable of receiving and acting upon alerts from a local health authority over a cellular network, a wireless local area network (LAN), and the like.

In another example, the present disclosure also includes a self-disinfecting touch screen point-of-sale system, e.g., at a retail store, restaurant or supermarket, which is touched by many people throughout a day. For instance, the point-of-sale system may sterilize a surface of the point-of-sale system as well as sterilize the fingers and hand of a person operating the touch screen utilizing a UV LED integrated within the touch screen.

In addition, examples of the present disclosure may be implemented within or in connection with other non-display touch technology-related surfaces, such as keyboards, mice, game controllers, joysticks, styluses, and so forth. For example, some keyboards include LEDs under the keys of the keyboard. Thus, in accordance with the present disclosure, one or more UV LEDs, e.g., emitting UV-C light at or around 207 nm, may be included within the keyboard. Accordingly, in one example when the keys are pressed, the UV LED is activated. Alternatively, or in addition, a UV LED, similar to an infrared emitter, may be deployed on the surface of the keyboard to expose the surface of the keys. In one example, a keyboard may be configured to utilize different intensities of light, different durations of activation and different activation schedules depending upon whether a person is actively utilizing the keyboard. For example, the UV light may be emitted with a higher intensity/shorter duration when the keyboard is in active use and a lower intensity/longer duration when the keyboard is not in use.

Similarly, with respect to computer mice, an integrated LED may be activated to continuously disinfect the mouse surface when the mouse is on, where the surface may be translucent to allow the occasion disinfection. When a mouse button is pressed, a hideaway LED may flash the user's fingertips. In another example, a center roller can be continuously disinfected inside the mouse. Moreover, the mouse pad is also considered a highly contaminated surface. Thus, in still another embodiment the mouse may include at least one UV LED directed downward at the mousepad (or tabletop) to effectively clean the surface as it is used.

The present disclosure also applies to non-computing devices such as shopping carts, tabletops, counters, cash register tills, door handles, door knobs, transportation lighting and so forth. For example, a shopping cart may include a UV LED embedded in the cart handle. The UV LED may be powered by one or more batteries, a solar panel or a microgenerator in the wheel(s) of the cart. In this regard, it should be noted that intelligent sterilization rules of the present disclosure may in one alternate embodiment be implemented by physical logic rather than by a computing device and/or processor. For example, a physical activity such as grasping an object, opening or closing a compartment, or setting an object in motion or placing it at rest may comprise a triggering event. It should also be noted that sterilization and disinfection is not limited to the handle of the cart, but affects any surface of the cart that may be exposed to the UV light. In addition, cash is passed around amongst many people, potentially many times a day, and when placed in a cash register, is stored in a confined space. Thus, in another example a cash register may include a UV LED embedded in the till/drawer. When the till is closed, the UV LED may be turned on such that the UV light covers all visible surfaces.

For transportation lighting, LED lighting replacing existing incandescent or florescent lighting could provide the disinfection in transportation areas, which are also vectors. In personal transportation, the dome light of a motor vehicle may be made to include a UV LED. In turn, the dome light may be configured to emit UV light for several seconds, e.g., after the motor vehicle is started, after a door is opened and/or closed, after a main cabin light is turned off (e.g., detected using a built-in capacitor with the functional circuitry designed into the bulb housing). Alternatively or in addition, a motor vehicle may be designed to include one or more UV LEDs in various locations with the intent to cover places such as the footwells, steering wheel, stick, and keys. In another example, the vehicle may include a system with one or more UV LEDs that are controlled to utilize different intensities of light, different durations of activation and different activation schedules depending upon whether a person is actively within the vehicle or operating the vehicle. For example, a driver's presence may be detected when a key is in the ignition, when the engine is running, when hands are detected on the steering wheel by an integrated sensor, and so forth.

The foregoing describes various exemplary devices and usages of such devices in accordance with the present disclosure. In this regard, it should be noted that all of the above described devices not only include at least one UV light source, but also include components to enable the intelligent activation of sterilizing UV light in response to various conditions. For example, various embodiments may emit sterilizing UV light in response to one or more detected conditions, e.g., presence of a surface to be disinfected and/or human presence (which may include the pressing of a key, touching of a touch screen, passing in front of a camera or other motion detector, etc.), presence of a device at a particular location, and so forth. Thus, in one embodiment an exemplary device may include at least a processor and a memory storing instructions to enable the processor to implement steps, functions and/or operations in connection with the intelligent activation of sterilizing UV light.

To aid in understanding the present disclosure, FIG. 1 illustrates in greater detail an exemplary system 100 that is suitable for use in conveying messages in support of intelligent sterilization of surfaces, according to the present disclosure. Although the present disclosure is discussed below in the context of a particular system or network architecture, the present disclosure is not so limited. Namely, the present disclosure can be applied to any type of communication network that is capable of transmitting data, such as a local area network (LAN), a wireless local area network (WLAN), an Internet Protocol (IP) network, such as an Internet Protocol/Multi-Protocol Label Switching (IP/MPLS) core network, an IP Multimedia Subsystem (IMS) network, communications over the Internet in general, and so forth.

As shown in FIG. 1, the system 100 connects a mobile device 190, or other device, such as a LED-backlit television (TV) 192, with one or more application servers via a core Internet Protocol (IP) network 110, a cellular access network 140, an access network 150 and/or Internet 180. In one embodiment, cellular access network 140 may comprise a radio access network implementing such technologies as: global system for mobile communication (GSM), e.g., a base station subsystem (BSS), or IS-95, a universal mobile telecommunications system (UMTS) network employing wideband code division multiple access (WCDMA), or a CDMA3000 network, among others. In other words, cellular access network 140 may comprise an access network in accordance with any "second generation" (2G), "third generation" (3G), "fourth generation" (4G), Long Term Evolution (LTE) or any other yet to be developed future wireless/cellular network technology. While the present disclosure is not limited to any particular type of wireless access network, in the illustrative embodiment, cellular access network 140 is shown as a UMTS terrestrial radio access network (UTRAN) subsystem. Thus, element 145 may comprise a Node B or evolved Node B (eNodeB).

In one embodiment, access network 150 may comprise a non-cellular access network such as a wireless local area network (WLAN), an IEEE 802.11 network, a "wired" access network, e.g., a local area network (LAN), an enterprise network, a metropolitan area network (MAN), a digital subscriber line (DSL) network, a cable network, a hybrid network utilizing a plurality of such technologies, and so forth. Thus, in one example access network 150 may include at least one wireless communication point 155, which may comprise a wireless access point/wireless router, an IEEE 802.11 access point, a ZigBee access point, a Bluetooth Low Energy (BLE) beacon, and so forth. In one example, access network 150 may include multiple wireless communication points 155 of different types. In one example, access network 150 may comprise a local network of a residence or business, e.g., a hospital, an enterprise network or the like. Thus, as illustrated in FIG. 1, mobile device 190 and TV 192 may have one or more wired or wireless connections to access network 150.

In one embodiment, mobile device 190 may comprise any endpoint device configured for wireless communication such as a personal computer, a laptop computer, a Wi-Fi device, a Personal Digital Assistant (PDA), a mobile phone, a smartphone, an email device, a computing tablet, a messaging device, and the like. In one embodiment, mobile device 190 may have both cellular and non-cellular access capabilities and may further have wired and/or wireless communication/networking capabilities.

In one embodiment, mobile device 190 includes an LED-backlit display, where the display may further comprise a touch screen. Notably, one or more LEDs incorporated into the backlighting may comprise a UV LED, e.g., emitting in the UV-C range, and/or at or about approximately 207 nm, for sterilization purposes. In one example, the mobile device 190 may also run an intelligent sterilization management application which enables the mobile device 190 to locally manage sterilization/disinfection functions, and/or to interact with an application server (AS) (e.g., any one or more of AS 120, AS 125 and AS 127) for receiving instructions, and for sending and receiving data/messages relating to sterilization functions. In one example, TV 192 (e.g., a smart TV which may include LED backlighting as well as an audience-facing camera) may also run an intelligent sterilization management application which enables the TV 192 to locally manage sterilization functions, and/or to interact with AS 120, AS 125 and/or AS 127, and so forth.

In one embodiment core IP network 110 comprises a telecommunication network service provider network with network devices or elements (not shown) which are capable of routing and forwarding IP packets between different hosts over the network. However, in one embodiment, the components of core IP network 110 may have additional functions, e.g., for functioning as a public land mobile network (PLMN)-General Packet Radio Service (GPRS) core network, for providing Voice over Internet Protocol (VoIP), Service over Internet Protocol (SoIP), and so forth, and/or may utilize various different technologies, e.g., Asynchronous Transfer Mode (ATM), Frame Relay, multi-protocol label switching (MPLS), and so forth. Thus, it should be noted that although core IP network 110 is described as an Internet Protocol network, this does not imply that the functions are limited to IP functions, or that the functions are limited to any particular network layer.

In one embodiment, the telecommunication network service provider may maintain an application server (AS) 120 in core IP network 110 for providing various services to the customer/mobile device 190 regarding sterilization functions. Alternatively, the network service provider (e.g., the owner and/or operator of core IP network 110) may maintain application server (AS) 120 on behalf of a hospital, a governmental health authority or similar organization. In this regard, the application server 120 may also include a database (DB) 121 for storing instructions and other information relating to sterilization functions in accordance with the present disclosure. For example, in one embodiment the information stored in DB 121 may include instructions for a sterilization schedule. For instance, the instructions may be provided to various devices such as mobile device 190 and TV 192, such that these devices may activate sterilization functions, or such that these devices may vary the intensities and/or temporal frequency of emission of the UV light used for sterilization depending upon the time of day, whether the presence of one or more people are detected in the same room or nearby to the device, and so forth.

In one embodiment, different instructions may be provided to different devices depending upon a particular location, e.g., a surgical suite, a neonatal intensive care unit or a burn ward, versus a reception desk, an area for outpatient physical therapy and the like. Alternatively or in addition, the information stored in DB 121 may include supplemental information to assist in managing sterilization functions. For example, DB 121 may maintain different disinfection schedules or other parameters for different device types, different locations, different users or other persons (e.g., doctors, nurses, patients, etc.) and so forth. In one example, DB 121 may store location data of various devices, device capability data, e.g., maximum intensities/light output levels, battery life information and/or information on whether the device has access to a power source, and so forth. In addition, DB 121 may maintain a list of specific locations and/or regions, such as areas where there is a disease outbreak or at least one known case of a pathogen based illness (broadly, a "disease event"), a list of hospitals, schools, fitness centers, supermarkets and similar types of public places where diseases can be transmitted. Thus, in one embodiment AS 120 may send messages and/or instructions to devices which are known to satisfy a particular location parameter, such as having a presence in one of the locations or regions in the list stored in DB 121, altering the devices to activate or increase sterilization functions locally on such devices. For example, if a health authority determines that there is a cluster of influenza cases in a particular area, the health authority may cause DB 121 to be updated to include this region in a list of regions of concern. For any device that is determined to be located in this region, AS 120 may send a message and/or instructions to enable the device to activate or increase sterilization functions. In any case, AS 120 may comprise any hardware server or computer that is well known in the art, and the database 121 may be any type of electronic collection of data that is also well known in the art. In addition, AS 120 may send information to and receive information from mobile device 190 and/or TV 192 via various communication paths such as via the cellular access network 140 or via the access network 150.

In still another embodiment, access network 150 may maintain its own application server, e.g., AS 127, for supporting sterilization services in accordance with the present disclosure. For example, access network 150 may comprise a local network of a hospital, a school, a fitness center, and so forth, which maintains and coordinates sterilization functions for various devices throughout the facility. Thus, in one embodiment, AS 127 may comprise any hardware server or computer that is well known in the art, and the database 128 may be any type of electronic collection of data that is also well known in the art. Accordingly, AS 127 may provide the same or substantially similar functions as AS 120, as described herein.

In still another embodiment an application server, e.g., AS 125, may be maintained "in the cloud", i.e., reachable via the Internet 180 in general. In one example, AS 125 is maintained by a hospital, or any other entity that is providing sterilization services, and/or performs operations controlled by the hospital or other entity. For example, AS 125 may be provided by a cloud service provider. In one embodiment, AS 125 may comprise any hardware server or computer that is well known in the art, and the database 126 may be any type of electronic collection of data that is also well known in the art. Accordingly, AS 125 may provide the same or substantially similar functions as AS 120, as described herein.

In one example, AS 120, AS 125 and/or AS 127 may individually or collectively perform various functions relating to sterilization services, in accordance with the present disclosure. For instance, AS 127 may transmit a sterilization schedule to mobile device 190 for implementation on the mobile device 190, but may receive instructions from a regional health authority regarding a disease outbreak in the area, e.g., from AS 120 or AS 125. As such, AS 127 may adjust the schedule and/or transmit a new sterilization schedule to mobile device 190. For instance, the schedule may call for more frequent activation of a UV light source, the use of greater intensities of light, and so forth. Other, further and different arrangements of the same or a similar nature are all contemplated within the scope of the present disclosure.

The above network 100 is described to provide an illustrative environment in which embodiments of the present disclosure may be employed. In other words, the network 100 is merely illustrative of one network configuration that is suitable for implementing embodiments of the present disclosure. Thus, the present disclosure may also include any other different network configurations that are suitable for implementing embodiments of the present disclosure, for conveying communications among endpoint devices, for conveying communications between endpoint devices and other components (e.g., core network and access network components), and so forth. In particular, embodiments of the present disclosure may be implemented in any wired or wireless communication environment and may implement any communication technologies and protocols that enable at least two devices to communicate, including: a cellular network, a wired and/or wireless local area network, a wide-area network, a wireless short-range peer-to-peer or mesh network, a satellite-based communication network, and Internet service provider access network, a layer 3 transport network, a combination of one or more of the foregoing network types, and so forth. Thus, those skilled in the art will realize that the communication system 100 may be expanded by including additional endpoint devices, access networks, network elements, application servers, etc., or modifying or substituting those illustrated in FIG. 1, without altering the scope of the present disclosure.

Figure 2A:
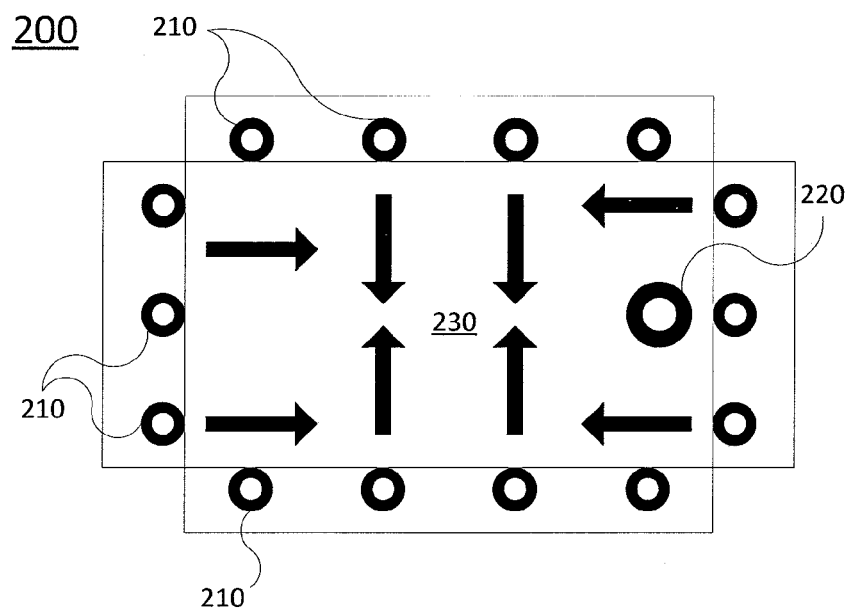
FIG. 2A illustrates a first exemplary scenario involving LED-backlit displays, the present disclosure is not so limited.

To further aid in understanding the present disclosure, FIG. 2A illustrates an exemplary device 200 for providing intelligent sterilization services. As shown in FIG. 2A, device 200 includes various LEDs 210 positioned along the edges of a display screen 230. In other words, device 200 comprises an edge-lit LED display. However, it should be noted that the present disclosure is not limited to edge-lit device, but may include devices having various configurations, such as an array-lit LED display. It should also be noted that for illustrative purposes, only a few of the LEDs 210 are specifically labeled in FIG. 2A. In one example, display screen 230 broadly includes a light guide, for directing light emitted by the LEDs 210 in a direction perpendicular to the display screen 230, a diffuser, a thin-film transistor (TFT) liquid-crystal display (LCD) and other components. In one example, device 200 integrates components supporting touch-screen technologies with display screen 230. For example, device 200 may comprise a tablet computing device, a smart phone and the like. In another example, device 200 may comprise a LED TV, e.g., a "smart TV", a point-of-sale touch screen terminal, or other device incorporating a LCD LED-backlit display.

Many LED backlighting arrangements utilize LEDs emitting a blue wavelength light in conjunction with a yellow phosphor, for approximating a white light. Other arrangements utilize red, green and blue LEDs to create a white light. The LEDs 210 of device 200 may incorporate either configuration. For example, each of the LEDs 210 may comprise one of a red, green or blue LED, or each LED 210 may comprise a composite LED with red, green and blue emitters in a single unit.

In any event, in accordance with the present disclosure at least one of the LEDs 210 comprises a UV LED emitting UV light, e.g., at or around 207 nm. Accordingly, device 200 may activate at least one UV LED based upon various factors including, whether the display screen 230 is currently being touched, whether a presence of one or more individuals is detected by the device 200, whether the device 200 is at a specific location, whether it is a scheduled time for activation, whether instructions received by the device 200 direct the activation at the current time, and so forth. For instance, as mentioned above, display screen 230 may incorporate touch screen technology such that it may be detected when the device 200 is currently being touched by a user. In one example, device 200 may also comprise a camera 220 which can be used in conjunction with image processing applications (e.g., face or flesh tone detection applications) to detect whether one or more individuals are present. In addition, device 200 may also have a wired or wireless connection to enable the device 200 to send and receive information relating to sterilization functions over one or more networks, e.g., to receive sterilization scheduling information from a hospital or other entity. In this regard, device 200 may also include components which enable the device 200 to react to its environment and to emit sterilizing UV light in an intelligent manner. For example, device 200 may be embodied in the form of system 600 described below, e.g., having a processor, a memory, etc.

When device 200 activates one or more UV LEDs, it is capable of sterilizing the surface of the display 230, e.g., the touch screen. However, the disinfection capabilities of device 200 are not limited to only surfaces of the device 200 itself. Rather, device 200 is capable of disinfecting any surfaces which are visible to the display screen 230. In particular, device 200 may disinfect at least a portion of a human body when the presence of the portion of the human body is detected. For instance, device 200 may activate at least one UV LED to disinfect a finger or hand when it is detected that the touch screen is being touched.

Figure 2B:
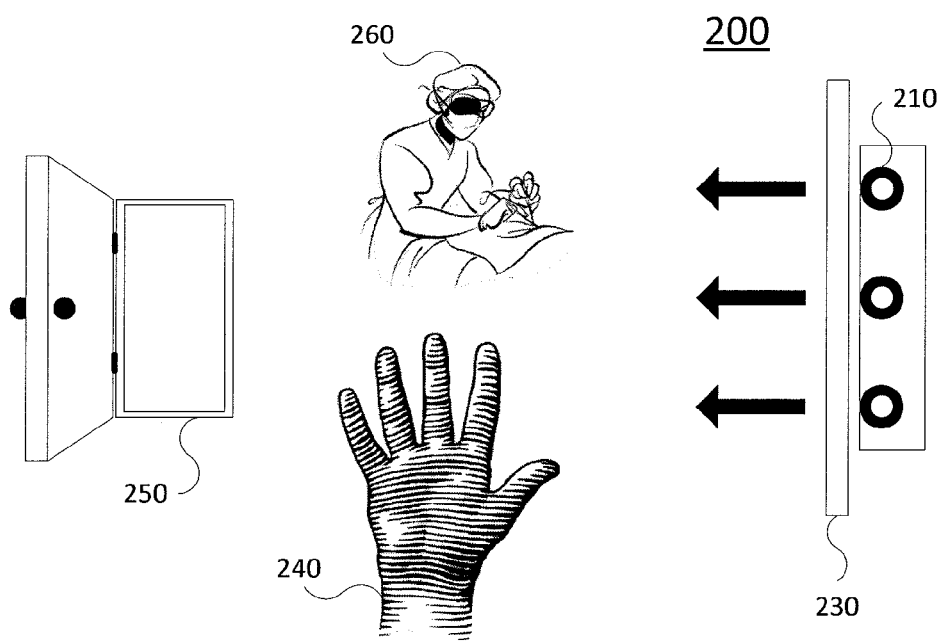
FIG. 2B illustrates a second exemplary scenario involving LED-backlit displays, the present disclosure is not so limited.

FIG. 2B illustrates several exemplary scenarios where device 200 (shown in a side/profile view) is utilized to disinfect part of a user's body, e.g., one or more fingers of a hand 240, objects, e.g., door 250, and at least one person 260 located near the device 200. For example, device 200 may comprise a TV in a hospital waiting room, surgical area, etc., and can be used to disinfect chairs, tables, doors and various other surfaces and/or objects.

Figure 2C:
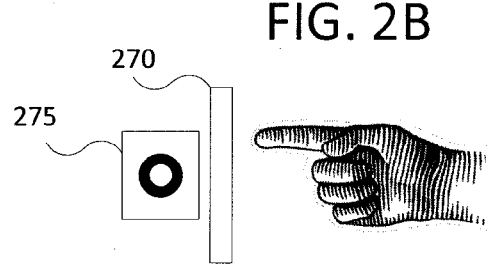
FIG. 2C illustrates an exemplary keyboard key having a UV LED for a backlight.

Although FIGS. 2A and 2B illustrate exemplary scenarios involving LED-backlit displays, the present disclosure is not so limited. For example, other, further, and different embodiments may include UV LEDs in non-display devices such as a keyboard or a mouse, a remote control, a shopping cart handle, a door handle, a tabletop, a countertop, in a dome light of a motor vehicle and so forth. For example, FIG. 2C illustrates an exemplary keyboard key 270 having a UV LED 275 for a backlight. In one embodiment, when the keyboard key 270 is pressed, the UV LED 275 temporarily activates to disinfect/sanitize the key as well as the finger pressing the key. In one example, the UV LED 275 is built in to an existing LED backlight for the key/keyboard. It should be noted that for non-display embodiments of the present disclosure, it is still necessary for the UV LEDs, or other UV light source to be connected to an intelligent device that is able to react to the environment and to emit sterilizing UV light in an intelligent manner, e.g., based upon a time of day, instructions which include a UV disinfecting schedule, based upon a touch detection, motion sensing or facial recognition by a camera in conjunction with a processor, and so forth.

Figure 3:
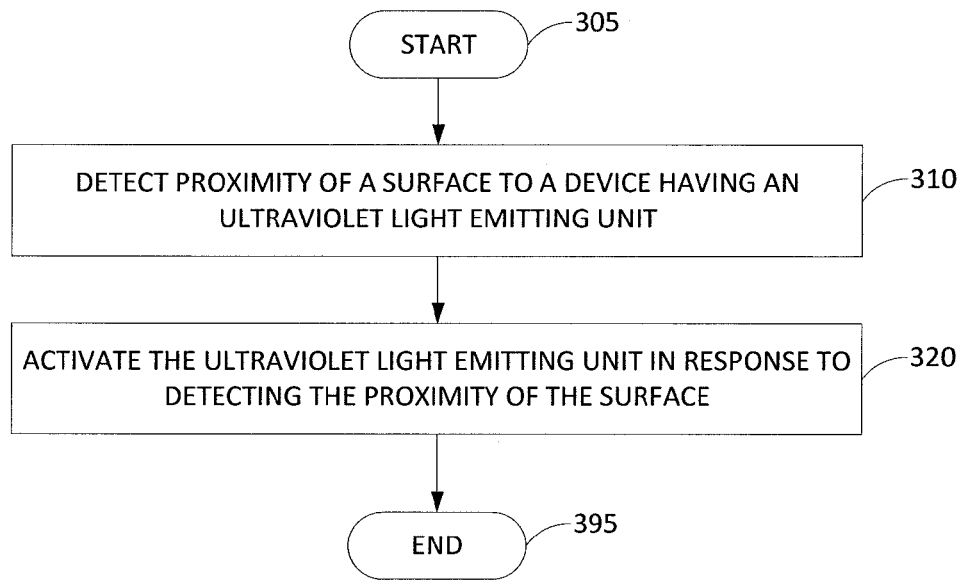
FIG. 3 illustrates a flowchart of a method for sterilizing a surface, according to one embodiment of the present disclosure.

FIG. 3 illustrates a flowchart of a method 300 for sterilizing a surface. In one embodiment, the method 300 is performed by a device such as any of devices 190, 192 or 200 of FIGS. 1 and 2. Alternatively, or in addition, the steps, functions, or operations of method 300 may be performed by a device or system 600, and/or processor 602 as described in connection with FIG. 6 below.

Method 300 starts in step 305 and proceeds to step 310.

In step 310, method 300 detects a proximity of a surface to a device having an ultraviolet light emitting unit. In one embodiment, the surface comprises at least a portion of human body, e.g., a finger, a hand, a face, etc. In one embodiment, the proximity of the surface is detected via a sensor that is part of the device or is connected to the device. For example, the device may comprise a tablet computing device or other touch screen-based device that is operated by a user. Accordingly, the method 300 may detect that the user's finger is touching the screen of the device. In another example, the method may sense the presence of a user in another way. For example, the device may comprise a laptop or desktop computer with a mouse and/or a keyboard, a cash register, and so forth. Thus, the method may detect the presence of the user when the user operates the mouse or presses a key. Similarly, the device may comprise a door handle, a shopping cart handle, or other handle with a built-in UV LED and a heat sensor or touch sensor by which the method 300 may detect that the handle is being touched, turned, pushed and so forth.

It should be noted that various other types of sensors may be used to detect the presence of a surface in accordance with the present disclosure. For example, the method 300 may detect the presence of a person or other object/surface via a camera, if the device is so equipped. For instance, the device may comprise a smart TV, a personal computer, laptop, tablet, smartphone and the like, with a built-in or attached camera. Accordingly, the camera may be utilized as a motion sensor, or may be used to capture images from which the method may perform facial detection or the like. In still other embodiments, the presence of the surface may be detected using a heat sensor, a magnetic sensor, and so forth. For example, the device may comprise a point-of-sale terminal with a credit card reader having a built-in UV LED. Thus, the surface may comprise a credit card that may be detected at step 310 when it is swiped through the card reader. Alternatively, or in addition, the surface to be sterilized may be considered to be the hand of the operator, where the presence of the hand is detected by the card swipe.

At step 320, the method 300 activates the ultraviolet light emitting unit in response to detecting the proximity of the surface at step 310. For example, if the device comprises a touch-screen device, the method 300 may activate a UV LED that is built-in to the backlighting. Notably, the ultraviolet light emitting unit may irradiate the finger or hand of the user using UV light in a frequency range that is non-damaging to human cells. For example, the UV light may be in part of the UV-C range, e.g., 190-225 nanometers, and more specifically at approximately 207 nanometers.

In another example, the device may have an external-facing UV LED that is activated at step 320. For example, many smartphones have external-facing LEDs with one or more colors for use in presenting different notifications, e.g., new text messages and emails, a phone call, a new voicemail, and the like, as well as for use as a flashlight. Thus, in one embodiment the external facing LED(s) may include a UV LED emitting in the abovementioned range of wavelengths which can be activated at step 320. Similarly, in the case where the device comprises a credit card reader, the reader may include one or both of a UV LED within the reader (to irradiate the card) and an external-facing UV LED to irradiate the user's hand. In the case where the device comprises a door handle or the like, the device may be clear or sufficiently translucent to pass UV light in the abovementioned range. In addition, such a device may include an internal UV LED that when activated at step 320, can irradiate a hand that is touching the device. It should be noted that various other devices as described herein may be modified to include an internal or external facing UV LED that may be activated at step 320. Following step 320, the method 300 proceeds to step 395 where the method ends.

Figure 4:
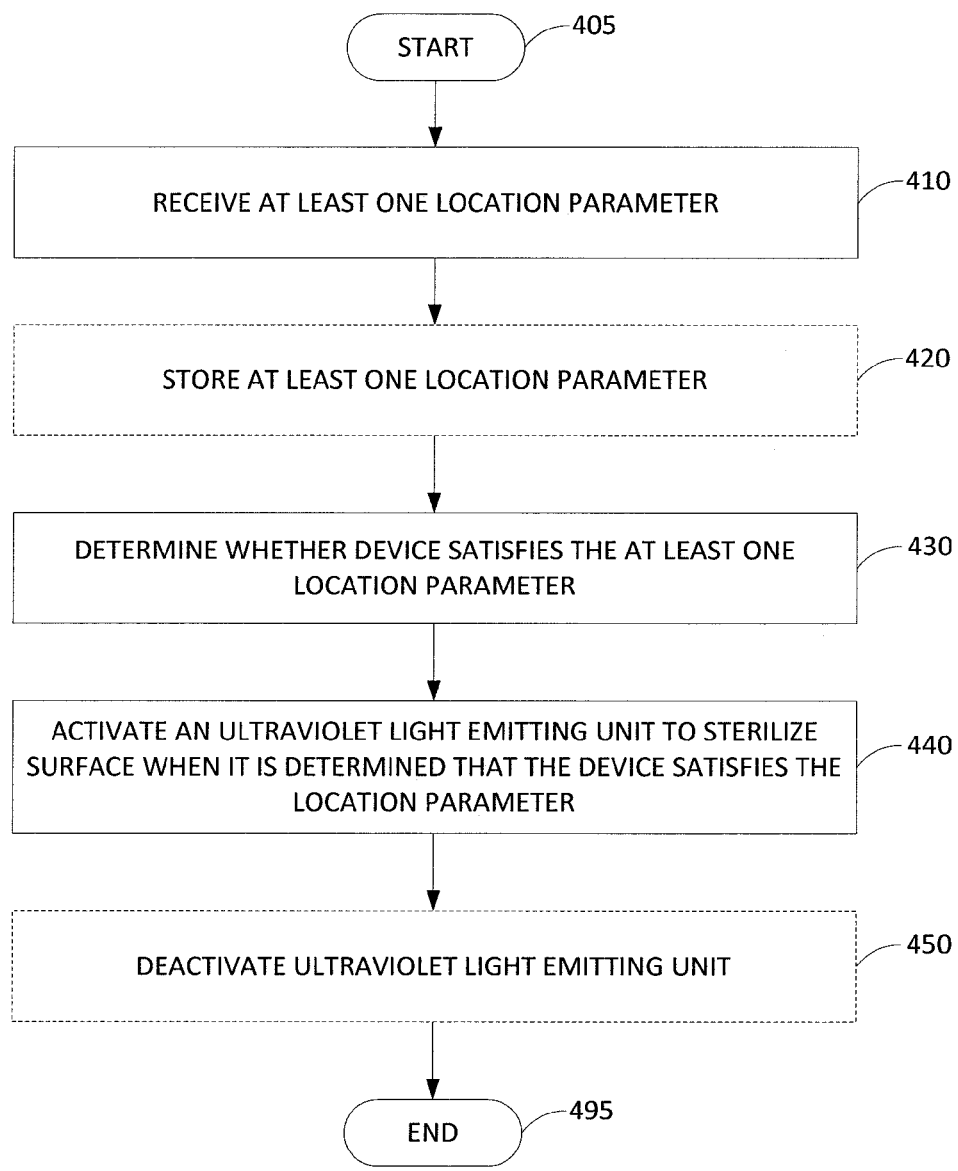
FIG. 4 illustrates a flowchart of an additional method for sterilizing a surface, according to one embodiment of the present disclosure.

FIG. 4 illustrates a flowchart of an additional method 400 for sterilizing a surface. In one embodiment, the method 400 is performed by a device such as any of devices 190, 192 or 200 of FIGS. 1 and 2 which has a UV light emitting unit. Alternatively, or in addition, the steps, functions, or operations of method 400 may be performed by a computing device or system 600, and/or processor 602 as described in connection with FIG. 6 below.

Method 400 starts in step 405 and proceeds to step 410. In step 410, method 400 receives at least one location parameter. For example, the location parameter may comprise a condition relating a location of a user, and more particularly to a location of the device of the user. The location parameter may also be associated with a corresponding action. For example, the location parameter may comprise a condition that the device is present at a specified location, or is connected to, or is detecting a wireless signal from a particular wireless beacon. The associated action may be an activation of a UV light, or a deployment of a particular UV light schedule. In one example, the location may be known to be a current site where a disease is being spread, broadly a location of a "disease event", such as in a school where it is known that a number of staff and students are currently suffering from influenza, a hospital with an outbreak of staph infection, and the like. However, in another example, the location may simply be a place that is a risk factor for disease transfer, such as a hospital, a school, a library, a supermarket or other public place where it is expected that many people will be touching and interacting with the same devices and objects, such as shared computers, point-of-sale terminals, doors, shopping cart handles, money, credit cards, and so forth.

In various examples, the location associated with the location parameter may comprise a more specific or a more general area. For example, in one embodiment, the location parameter may comprise a condition that a device is located on, within or near a particular floor or a particular ward of a hospital. In another embodiment, the location parameter may be a condition that the device is present near or in a particular town, county, state, metro area or other region. In one embodiment, the location parameter may be specified by geofencing, e.g., that the device is within a specified distance from a particular point, e.g., within 10 miles from the center of a city.

As mentioned, in one embodiment the location parameter may be associated with a connection to or detection of a wireless signal from a particular wireless beacon such as a WLAN access point, cellular base station, RFID beacon, BLE beacon and so forth. For example, the location parameter may nominally comprise a condition that the device is present at a hospital. However, in practical implementation the location parameter may be specified as a condition that the device is connected to a WLAN access point associated with the hospital. Similarly, the location parameter may comprise a condition that the device is detecting a particular BLE beacon, from which signals may be sufficiently localized such that the signals are received only by devices within a particular ward of a hospital.

In one embodiment, one or more location parameters are received at step 410 from a user of the device. For example, the user may manually populate a list of location parameters. Alternatively, or in addition, at step 410 the method 400 may receive one or more location parameters via one or more notification messages. The method 400 may then store such location parameters locally on the device. For example, an application server deployed in a local network, or a service provider network-based or internet-based application server may store various location parameters and transmit these location parameters to various devices under various circumstances. For example, an application server at a hospital may send broadcast notification messages comprising the location parameter via one or more BLE beacons deployed in and around the hospital such that any listening device will receive the location parameter. In another example, an application server may send broadcast messages via a number of cellular base stations, e.g., in a given city or region, such than any listening device within range of one of the cellular base stations may receive the notification message. Similarly, an application server may send individualized notification messages to particular devices via one or more networks such as illustrated in FIG. 1.

At optional step 420, the method 400 stores at least one location parameter. For example, a location parameter may comprise a rule or condition pertaining to a location of the device. In some cases, the device will not satisfy the location parameter at the time when the location parameter is first received, e.g., as step 410. Thus, the method 400 may store the location parameter on the device such that the method 400 may later check whether the location parameter is satisfied as the device and the user move from location to location during a day, a week, etc.

At step 430, the method 400 determines whether location information of the device satisfies the location parameter. The location parameter comprises a condition that the device be present at a particular location. Thus, in one example step 430 may comprise determining location information of the device, e.g., using GPS function of the device or using cellular or wireless network connection information. In one example, step 430 may include detecting a wireless signal from a particular wireless beacon, such as a signal from a particular WLAN access point, cellular base station, RFID or BLE beacon, and so forth. Notably, in one embodiment the receiving of a location parameter at step 410 may automatically result in a determination that the location information of device satisfies the location parameter at step 430. For example, a hospital may send a broadcast message or individual message to any device within range of, or connecting to its wireless network to indicate that sterilization functions should be activated or increased. Thus, upon receiving the message, the method 400 may automatically determine that the location information of the device satisfies the location parameter, e.g., by virtue of the fact that it is connected to the hospital's wireless network.

At step 440, the method 400 activates an ultraviolet light emitting unit to sterilize the surface when it is determined that the location information of the device satisfies the location parameter. In one embodiment, step 440 may comprise turning on a UV light emitting unit that was previously inactive. In another example, step 440 may comprise activating the UV light emitting unit more frequently and/or using a greater intensity light, or increasing the duration of use of the UV light source in a predefined period of time. In one embodiment, the UV light emitting unit activated at step 440 may comprise a UV LED that is part of a backlighting of a screen of the device. In another embodiment, the UV light emitting unit comprises an externally-facing UV LED of the device. In addition, in one example, the UV light emitting unit may emit UV light in the UV-C range that is non-damaging to human cells, e.g., in the range of 190-225 nanometers. In one embodiment, the UV light emitting unit emits at approximately 207 nanometers.

In one embodiment, aspects of the activation at step 440 may be based upon actions or instructions associated with the location parameter/condition. For example, a notification message received at step 410 may include a location parameter/condition and a corresponding action to take when the location information of the device satisfies the location parameter. However, in another example, aspects of the activation at step 440 may be based upon alternative or additional criteria. For example, if the battery of the device is low, the method 400 may select to emit UV light with less frequency and/or with less intensity, notwithstanding that satisfying the condition may otherwise call for a more increased intensity or a more frequent activation.

In one embodiment, the surface to be sterilized comprises at least one surface of the device. For example, the surface may comprise a LCD touch screen, where the UV light emitting unit activated at step 440 may comprise a UV LED that is part of a backlighting of the touch screen. In another embodiment, the surface may comprise a keyboard, e.g., of a laptop or portable computer. In still another embodiment, the surface to be sterilized comprises a portion of a human body, e.g., finger(s) and/or a hand of a user of the device. For example, the activation may not result in immediately turning on the UV light source, but may instead comprise activating a feature of the device where the UV light source is selectively turned on in response to a user's touch, a detection of a user's proximity to the device, and so forth. In this regard, step 440 may incorporate one or more aspects of the method 300 described above.

At optional step 450, the method 400 may deactivate the UV light emitting unit, or may deactivate a particular UV light activation schedule and revert to a previous schedule, or change to a different schedule. For example, if the condition/location parameter comprises a presence of a device at a particular location, then step 450 may be triggered by the method 400 detecting that the device is no longer present at the location. For example, GPS coordinates of the device may indicate that the device is no longer present in the specified area, the device may lose connectivity to a particular network or access point, and so forth. Following step 440 or 450, the method 400 proceeds to step 495 where the method ends.

Figure 5:
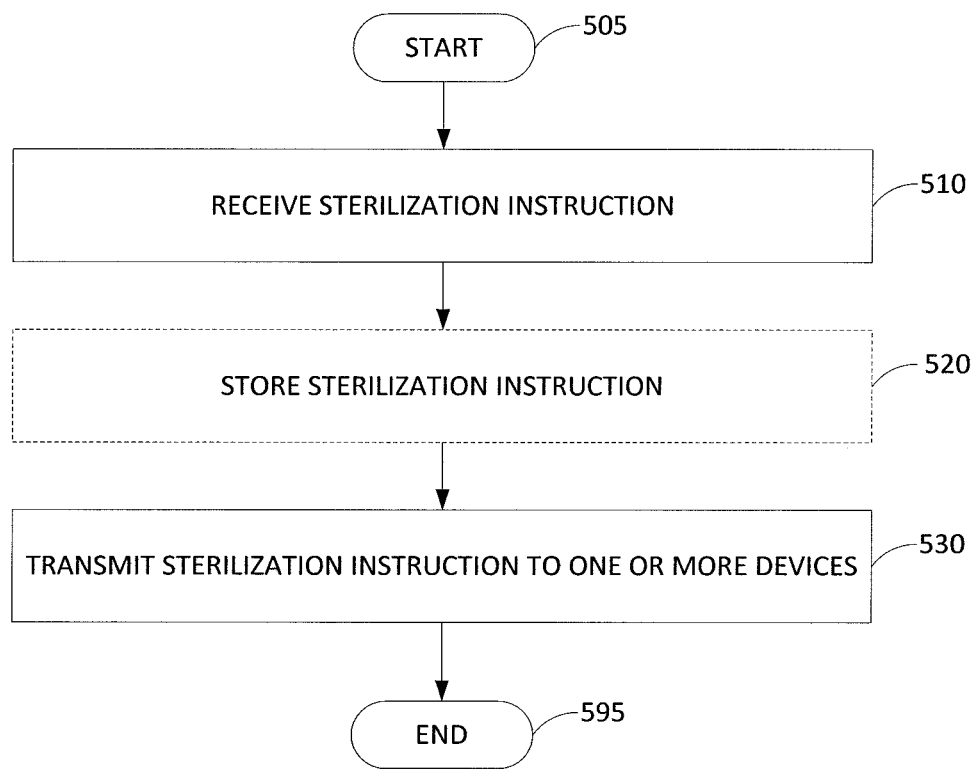
FIG. 5 illustrates a flowchart of another method for sterilizing a surface, according to one embodiment of the present disclosure.

FIG. 5 illustrates a flowchart of a method 500 for sterilizing a surface. In one embodiment, the method 500 is performed by an application server, such as any of application servers 120, 125 and 127 in FIG. 1. Alternatively, or in addition, the steps, functions, or operations of method 500 may be performed by a device or system 600, and/or processor 602 as described in connection with FIG. 6 below.

Method 500 starts in step 505 and proceeds to step 510. In step 510, method 500 receives a sterilization instruction. In one embodiment, the sterilization instruction may relate to a particular device, or class of devices, and/or a particular location. For example, the sterilization instruction may comprise an instruction to activate to activate or increase the usage and/or intensity of UV light source(s) locally on one or more devices. In one example, the sterilization instruction is received as a user input. For example, a hospital or school administrator may input a sterilization instruction that is received by the method 500 at step 505. Alternatively, or in addition, the method 500 may receive a sterilization instruction from an external device, e.g., from another server associated with a regional health authority or the like. In one example, the sterilization instruction may be related to a disease event. However, in another embodiment, the sterilization instruction may be related to a user of a particular device. For example, the sterilization instruction may be specified to be applicable to one or more users in a particular class. For example, a doctor or hospital discharging patients who have recently had surgery or been treated for wound or burns, who have catheters installed, and so forth may prescribe increased sterilization to be scheduled. Accordingly, via method 500, the devices of such patients may be caused to deploy a particular sterilization schedule as determined by a physician or other medical staff.

In one example, the sterilization instruction may include a sterilization schedule. In one embodiment, different sterilization schedules may be specified depending upon whether the presence of a user is detected, depending upon different battery levels of a local device, and so on. Alternatively, or in addition, in one example the sterilization instruction may have a location-dependent component. For example, the sterilization instruction may comprise a location parameter, e.g., having a location condition and an action, for use by one or more devices. For example, the sterilization instruction may be applicable to one, several or all devices located at or near a hospital, located in a particular city and so forth.

At optional step 520, the method 500 stores the sterilization instruction. For example, the sterilization instruction may be applicable to devices which are located at or near a particular location, e.g., a hospital. Thus, the method 500 may wait until it is determined that a device is present at the hospital before sending the sterilization instruction. In addition, since many users (and their devices) may potentially be coming and going from the hospital throughout the day, the method 500 may store the sterilization instruction for an indefinite period of time since it may be necessary to send the sterilization instruction to different devices at different times.

At step 530, the method 500 transmits the sterilization instruction to one or more devices. For example, a notification message comprising the sterilization instruction may be sent to a device, or may be broadcast to multiple devices. In one embodiment, the notification message is sent at the time it is received at step 510, or soon thereafter. For example, the sterilization instruction may relate to a disease event that is presently occurring. Thus, it may be desirable that the notification message be sent without delay. However, in another embodiment, the sterilization instruction may be sent when the method 500 determines that a device (e.g., a device with a particular identification code) satisfies a particular condition (e.g., the device is at a location specified in a location parameter). For instance, the device may continuously or periodically transmit location information to the method 500, such that the method can determine the current location of the device. In another embodiment, the method 500 may continuously or periodically broadcast the notification message, e.g., via a WLAN access point, a cellular base station, etc. In this regard, it should be noted that the notification message may be sent using any one or more aspects of the network 100 illustrated in FIG. 1. Following step 530, the method 500 proceeds to step 595 where the method ends.

It should be noted that the foregoing describes representative methods for sterilizing a surface in accordance with the present disclosure. However, other, further and different embodiments of the same or a similar nature may also be provided in accordance with the present disclosure. For example, in another method, a user device may send its location information to a network-based server which determines whether the device satisfies any one or more location parameters. If so, the network-based server may then send instructions to the device to active a UV light source or to activate a particular UV light activation schedule. In addition, various types of portable device and surfaces other than those specifically mentioned may be the subject of the respective methods 300-500. For example, a patient's portable dialysis equipment may include at least one UV light emitting unit and computing components which may execute operations of the method 400. Thus, the method 400 may operate to sterilize at least one surface of the portable dialysis equipment, e.g., when the patient enters a hospital, doctor's office, library, etc.

In addition, although not specifically specified, one or more steps, functions or operations of the respective methods 300-500 may include a storing, displaying and/or outputting step as required for a particular application. In other words, any data, records, fields, and/or intermediate results discussed in the method can be stored, displayed and/or outputted either on the device executing the method or to another device, as required for a particular application.

Furthermore, steps, blocks, functions or operations in any of FIGS. 3-5 that recite a determining operation or involve a decision do not necessarily require that both branches of the determining operation be practiced. In other words, one of the branches of the determining operation can be deemed as an optional step. Furthermore, steps, blocks, functions or operations of the above described method(s) can be combined, separated, and/or performed in a different order from that described above, without departing from the example embodiments of the present disclosure.

Figure 6:
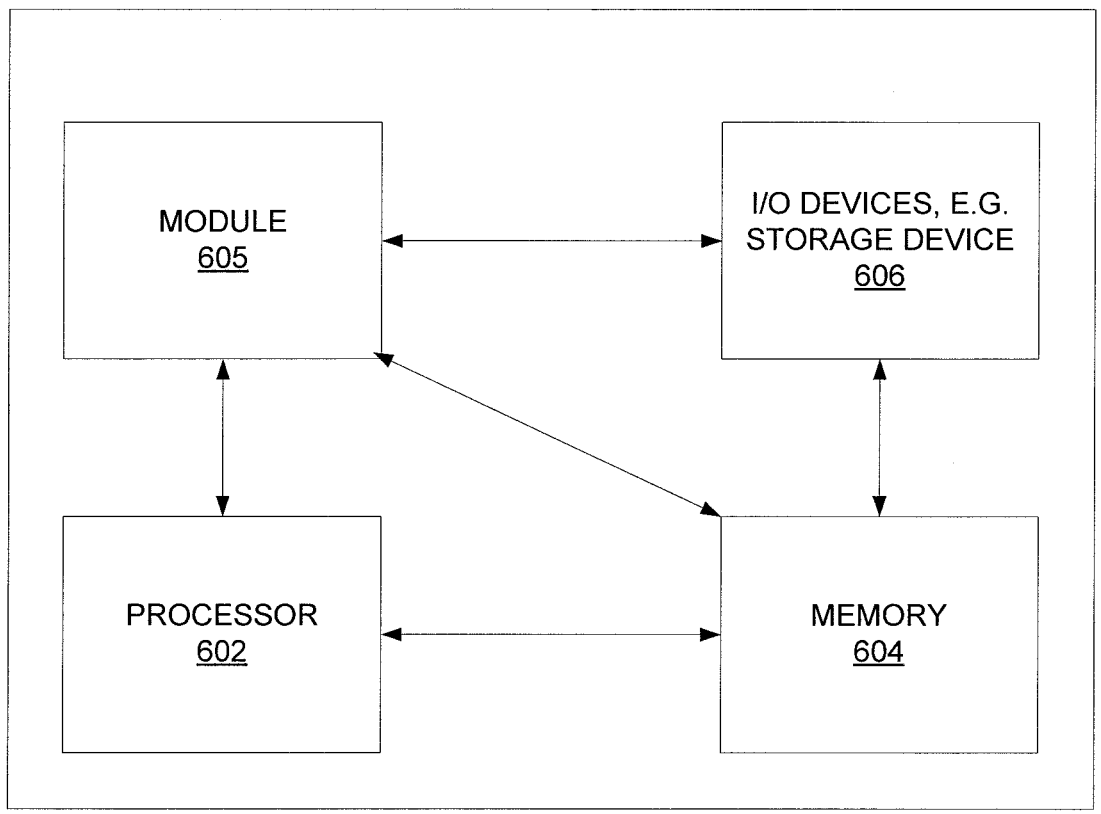
FIG. 6 illustrates a high-level block diagram of a general-purpose computer suitable for use in performing the functions, methods and algorithms described herein.

FIG. 6 depicts a high-level block diagram of a general-purpose computer suitable for use in performing the functions described herein. As depicted in FIG. 6, the system 600 comprises one or more hardware processor elements 602 (e.g., a central processing unit (CPU), a microprocessor, or a multi-core processor), a memory 604, e.g., random access memory (RAM) and/or read only memory (ROM), a module 605 for sterilizing a surface, and various input/output devices 606 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). In accordance with the present disclosure input/output devices 606 may also include a camera, various types of sensors, such as a magnetic sensor, a heat sensor, etc., and a UV light emitting unit, e.g., a UV LED. Although only one processor element is shown, it should be noted that the general-purpose computer may employ a plurality of processor elements. Furthermore, although only one general-purpose computer is shown in the Figure, if the method(s) as discussed above is implemented in a distributed or parallel manner for a particular illustrative example, i.e., the steps of the above method(s) or the entire method(s) are implemented across multiple or parallel general-purpose computers, then the general-purpose computer of this Figure is intended to represent each of those multiple general-purpose computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a general purpose computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 605 for sterilizing a surface (e.g., a software program comprising computer-executable instructions) can be loaded into memory 604 and executed by hardware processor element 602 to implement the steps, functions or operations as discussed above in connection with the exemplary methods 300-500. Furthermore, when a hardware processor executes instructions to perform "operations", this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 605 for sterilizing a surface (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A device for sterilizing a surface, comprising:
   an ultraviolet light emitting unit;
   a processor; and
   a computer-readable medium storing instructions which, when executed by the processor, cause the processor to perform operations, the operations comprising:
      detecting a proximity of the surface to the ultraviolet light emitting unit, wherein the proximity of the surface is detected without contacting the surface; and
      activating the ultraviolet light emitting unit to sterilize the surface in response to the detecting.

2. The device of claim 1, wherein the surface comprises a portion of a human body.

3. The device of claim 2, wherein the ultraviolet light emitting unit comprises a light emitting diode.

4. The device of claim 3, wherein the ultraviolet light emitting unit emits light at a wavelength of 207 nanometers.

5. The device of claim 2, further comprising:
   a sensor for detecting the proximity of the surface to the device.

6. The device of claim 1, wherein the device comprises a keyboard, a keypad, a mouse or a touch screen.

7. A device for sterilizing a surface, comprising:
   an ultraviolet light emitting unit;
   a processor; and
   a computer-readable medium storing instructions which, when executed by the processor, cause the processor to perform operations, the operations comprising:
      receiving a location parameter;
      determining whether location information of the device satisfies the location parameter; and
      activating the ultraviolet light emitting unit to sterilize the surface when it is determined that the location information of the device satisfies the location parameter and the location information indicates the device is not contacting the surface.

8. The device of claim 7, wherein the surface comprises a portion of a human body.

9. The device of claim 7, wherein the ultraviolet light emitting unit comprises a light emitting diode.

10. The device of claim 9, wherein the ultraviolet light emitting unit emits light at a wavelength of 207 nanometers.

11. The device of claim 7, wherein the location parameter is received wirelessly.

12. The device of claim 7, further comprising:
storing the location parameter in the computer-readable medium.

13. The device of claim 7, wherein the location parameter is associated with a disease event.

14. The device of claim 7, wherein the location parameter comprises:
a condition that specifies a presence at a specified location.

15. The device of claim 7, wherein the location parameter comprises:
a condition that specifies a connection to a particular wireless beacon.

16. The device of claim 7, wherein the activating comprises:
turning on the ultraviolet light emitting unit.

17. The device of claim 7, wherein the activating comprises:
increasing a duration of use of the ultraviolet light emitting unit in a predefined time period.

18. The device of claim 7, wherein the activating comprises:
increasing an intensity of an output of the ultraviolet light emitting unit.

19. A method for sterilizing a surface, comprising:
receiving, by a processor of a device, a location parameter;
determining, by the processor, whether location information of the device satisfies the location parameter; and
activating, by the processor, an ultraviolet light emitting unit to sterilize the surface when it is determined that the location information of the device satisfies the location parameter and the location information indicates the device is not contacting the surface.

20. The method of claim 19, wherein the surface comprises a portion of a human body.

* * * * *